United States Patent
Cobb et al.

(10) Patent No.: US 7,037,068 B2
(45) Date of Patent: May 2, 2006

(54) WARM AIR BLOWER FOR MEDICAL WARMING BLANKETS

(75) Inventors: Christopher B. Cobb, Hanover, MA (US); William E. Frey, Kingston, MA (US)

(73) Assignee: Level 1, Inc., Rockland, MA (US)

( * ) Notice: Subject to any disclaimer, the term of this patent is extended or adjusted under 35 U.S.C. 154(b) by 38 days.

(21) Appl. No.: 10/693,159

(22) Filed: Oct. 24, 2003

(65) Prior Publication Data

US 2004/0153132 A1   Aug. 5, 2004

Related U.S. Application Data

(60) Provisional application No. 60/428,488, filed on Nov. 22, 2002.

(51) Int. Cl.
F01D 25/04   (2006.01)

(52) U.S. Cl. .................. 415/119; 415/206; 417/312; 417/423.1

(58) Field of Classification Search ............ 415/47, 415/121.2, 119, 204, 206, 175–177, 196, 415/197; 417/312, 423.1
See application file for complete search history.

(56) References Cited

U.S. PATENT DOCUMENTS

| | | | |
|---|---|---|---|
| 2,110,022 A | 3/1938 | Kliesrath | |
| 2,601,189 A | 6/1952 | Wales, Jr. | |
| 3,193,193 A * | 7/1965 | Gerteis | 417/312 |
| 5,283,918 A * | 2/1994 | Weingartner et al. | 297/452.21 |
| 5,733,320 A | 3/1998 | Augustine | |
| 5,785,723 A * | 7/1998 | Beran et al. | 607/104 |
| 6,039,532 A * | 3/2000 | McConnell | 415/119 |
| 6,143,020 A | 11/2000 | Shigezawa et al. | |
| 6,254,337 B1 * | 7/2001 | Arnold | 415/119 |

* cited by examiner

Primary Examiner—Edward K. Look
Assistant Examiner—Devin Hanan

(57) ABSTRACT

An improved warm air blower system for providing a compact source of pressurized air that can be utilized for delivering warm or ambient air to a patient through, for example, a warming blanket. The warm air blower system can include a compression unit and a plenum chamber having a plenum member with a curvilinear interior surface, the plenum member interior surface has a plurality of surface indentations to enable the formation of controlled local turbulence adjacent the interior surface to reduce friction and noise as the compressed air moves across the interior surface. The warm air blower system can be appropriately mounted on a vertical pole, bed, stand or floor mounted. Air filters can be used to filter the air before and after induction to the compression unit. The safe operation of the warm air blower system is appropriately controlled and monitored by a control unit that includes a thermostat.

21 Claims, 14 Drawing Sheets

RESULTS OF NOISE TESTS

| EQ5000 NOISE AT FRONT(dB) | AIR SPEED (FEET/MINUTE) |
|---|---|
| 66.3 | 1600 |
| 65.5 | 1650 |
| 66.1 | 1700 |
| 66.0 | 1750 |
| 66.1 | 1800 |
| 67.0 | 1850 |
| 67.5 | 1900 |
| 67.2 | 1950 |
| 68.2 | 2000 |
| 68.9 | 2050 |
| 70.0 | 2100 |

SW4000 NOISE AT FRONT : 71.8 dB at AIR SPEED : 2040 feet/minute

*FIG. 13*

WARM AIR BLOWER FOR MEDICAL WARMING BLANKETS

The present application is based on a provisional application Ser. No. 60/428,488 filed on Nov. 22, 2002.

FIELD OF THE INVENTION

The present invention addresses a need to provide a blower system with testing features for delivering warm air to a patient in a medical environment, and more particularly to a low noise, high output compact blower.

DESCRIPTION OF THE RELATED ART

Various forms of warm air blowers have been utilized to inflate hollow medical blankets formed of layered sheets of paper, plastic or fabric for delivering heated air to a patient during surgery, recovery, or thermal treatment. Standard blowers with a smooth vortex can deliver air to a patient, and when increased air flow is required, the conventional design approach has been to provide a larger motor, fan, and/or plenum.

When a standard blower circulates air, the blower pulls in air through an impeller, blade or cage and then forces the air past the blade to change pressure from a negative to a positive force. As the air travels beyond the blade, it is compressed and its subsequent expansion can contribute to the generation of noise. Such noise can develop patterns of harmonic vibrations.

Thus, there is still a need to provide a smaller compact warm air blower with equivalent performance capabilities to a larger air blower, and/or at reduced noise levels.

SUMMARY OF THE INVENTION

It is an object of the present invention to provide a compact and efficient air blower system with a reduction in the generation of noise. A blower of the present invention can include a compression unit for compressing and directing air flow. The compression unit is connected to a plenum chamber for receiving the compressed air from the compression unit.

The plenum chamber has a plenum member with a curvilinear surface forming an interior wall of the plenum chamber. The plenum member has irregular indented sections to allow the air that is being compressed to expand locally and create in effect an air bearing, or localized turbulent air flow pattern of a controlled nature, to reduce the resistance to the movement of the air and to reduce the amount of energy required by the system while reducing the generation of noise.

If too much local turbulence is introduced, it would be counter-productive to the purposes of the present invention. The configuration of the plenum is further designed to disrupt noise with a harmonic component, by varying both the depth of individual indentations as well as the frequency and/or distance between the indentations, to further lessen the generation of noise and to increase the efficiency of the system.

A plenum member forming an interior wall of the plenum chamber can be either removable or fixed (non-removable) within the plenum chamber in order to accommodate different manufacturing methods as well as to facilitate the formation of particular patterns of irregular indentations on the plenum member.

Where the plenum member is removable, it can be formed from a single piece of semi-rigid material and is suitable for roll-pressing, for example, with the desired indentation pattern and then placing within the plenum chamber. Alternatively, the plenum member can be cast or molded with the indentations.

In an additional embodiment, the plenum incorporates a heater directly in the plenum chamber to further provide a compact size. The heated air is supplied to a cooperative receiving unit such as a blanket for covering a patient during surgery or recovery.

A control unit, including a control circuit to monitor and set temperatures for a heater, is also implemented in an embodiment of the present invention. The control unit includes an over-temperature setting to provide an upper-limit for each selected temperature setting, for example, a relative 3° C. above the selected temperature.

The blower also allows the selection of ambient, unheated air. A non-relative 47° C. over-temperature limit is associated with the ambient temperature selection to thereby monitor a runaway heater condition during normal operation or an over-temperature test.

The over-temperature test can be initiated from a front control panel having appropriate buttons, switches, and visual LED display indicators. The over temperature test can be activated by holding a desired temperature select button until its indicator LED starts to flash sending the system into a thermal runaway condition.

At the trip point, when the upper-limit temperature for the selected temperature is reached, the temperature meter display holds the trip temperature reading until the warm air blower is reset. An under temperature indication is associated with each temperature setting selected and is a relative 3° C. below the selected setting.

A self test mode of operation is provided to enable a user to check the operability of the blower system prior to placing it into service with a patient. This self test procedure can check the following conditions: open or shorted temperature control measuring device (thermistor); open or shorted alarm sensing measuring device (thermistor); proper servo connection attached to the machine; proper hose connection to the air outlet; proper functioning of the alarm circuit; and the absence of heater current at power turn on.

The servo connection relates to a control feedback connection, including the sensing thermistor at the point of delivery of heated air to the patient, and the control circuit where the output of the sensing device is used to control the temperature of the heated air.

A detection circuit is provided to sense the heater current and provide a logic level output. This detection circuit can shut down the heater and blower if the heater fails. The detection circuit can detect an open circuit as a safety feature. A switch at the air outlet connector can detect the presence of the hose. A variable speed blower motor can be utilized and calibrated so that the output air speed can be consistent from unit to unit during manufacturing, or to achieve a variety of performance levels.

Various sensors can be attached, not only at the output of the blower system, but also at the delivery point to the patient to thereby provide temperature inputs to control the delivery of the desired thermally heated air to the patient.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 13 shows a table of results of noise comparison testing for a blower of the present invention using a particular indentation pattern with line-symmetric indentations.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the intention is intended to cover alternatives, modifications and equivalents, which may be included within the spirit and scope of the invention as defined by the appended claims.

Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Figure 1:
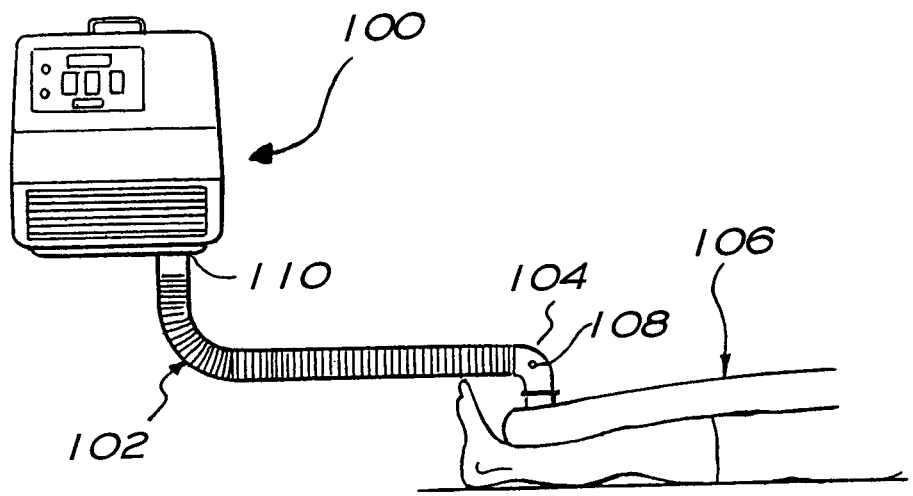
FIG. 1 shows the blower system, flexible conduit, and connecting elbow with temperature sensor mounted in close proximity to the cooperative receiving unit, in this embodiment a warming blanket, in order to accurately monitor the temperature of the air as it is delivered to the patient.

The present invention provides a compact air blower and heater assembly for delivering an efficient and controlled amount of heated air to a patient. In reference to FIG. 1, the output of the warm air blower system 100 can be connected to a flexible conduit 102, which in turn can be connected through an elbow 104 to a thermal blanket 106 of, for example, the type shown in U.S. Pat. No. 6,143,020, U.S. Pat. No. 5,733,320, U.S. Pat. No. 2,601,189, or U.S. Pat. No. 2,110,022.

The warm air blower assembly includes a control unit described infra. The control unit provides safety features including temperature control for pre-set temperature settings of 36° C., 40° C., and 44° C. The pre-set temperatures have an over temperature safety control level of a nominal 3° C. which, if violated, will cause the system to automatically cease heating and air blowing, and activate visual and audible alarms.

Figure 2:
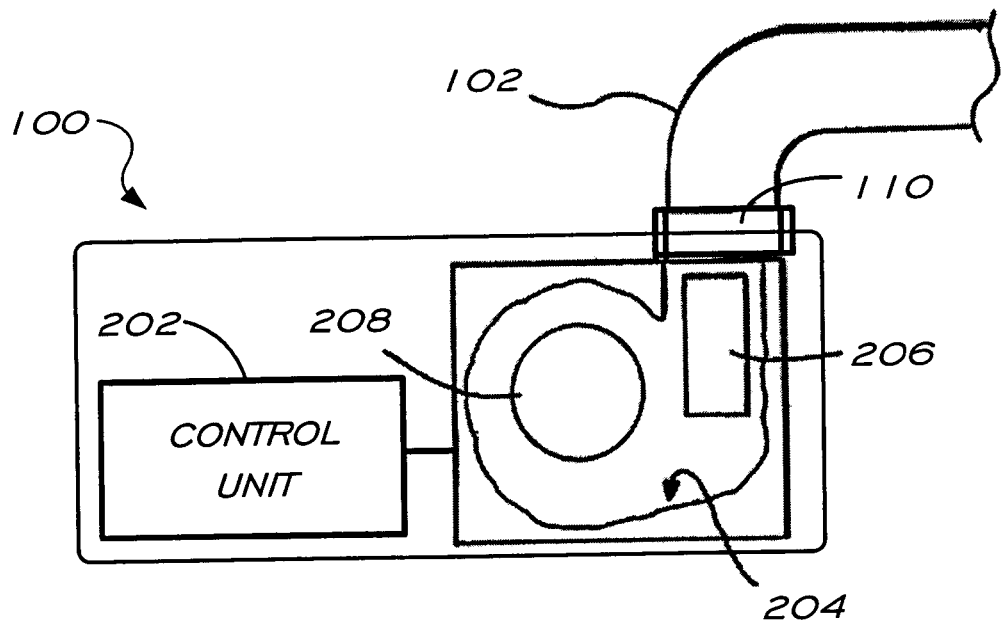
FIG. 2 shows a top view of the blower system showing the control unit, a plenum member having a curvilinear interior surface, a heater unit, and a compression unit with the flexible conduit attached to the rear portion of the blower system.

Generally, the fluctuation of set temperature will be less than ±1° C. The temperature of the delivered air is measured using a hose-end temperature thermistor 108 as a temperature sensor. Other sensors having a similar function may also be employed. The improper attachment of the flexible conduit 102 to the warm air blower system 100 is detected by a hose connection sensor 110, as shown schematically in FIG. 2. The hose connection sensor 110 can be a micro-switch suitably placed to detect the improper attachment of the flexible conduit 102 to the warm air blower system 100. As shown in FIG. 2, the flexible conduit 102 can be attached to a rear portion of the warm air blower system 100. Alternatively, the flexible conduit 102 can be attached to a side, top, front, or bottom portion of the warm air blower system 100 since the attachment location is not limited to the specific embodiment shown in FIG. 2.

The control unit 202 also provides an over-temperature setting corresponding to an ambient temperature or room temperature setting without heating. If the ambient temperature is selected and the delivered air temperature reaches 47° C., the system will automatically cease heating and air blowing.

An over temperature test capability is also provided wherein if a switch for setting a specific temperature is actuated for over eight seconds, the heater is energized and driven to a test procedure with the LED associated with the actuated button flashing to indicate a thermal runaway situation for test purposes. At the trip point of the thermal runaway for the corresponding set temperature, the meter display will hold the trip temperature reading until the system is reset by pressing the power off (standby) switch. In this specification, the terms button and switch are interchangeable and can refer to any actuator for use as described herein.

An under temperature control level is also provided for each temperature selection except for ambient, and it is also set to a nominal 3° C. below the selected setting. An under-temperature indicator on the front panel is activated when the delivered air temperature is below the under-temperature level for the selected set temperature. The over-temperature measurement detection is delayed following a reduction in the selected set temperature to allow the blower system enough time to adjust to the newly changed command level and avoid false alarm conditions.

A self-test circuit can be implemented before the system is put into operation so that comparators can be set with predetermined high and low values. The self-test circuit can detect an open or shorted temperature control thermistor, an open or shorted alarm sensing thermistor, and can verify a servo connection to the blower and heater assembly. A micro switch 110 can sense whether the flexible conduit 102 is improperly connected to the air outlet, thereby enabling the control unit to activate the disconnect indicator.

The servo connection relates to a control feedback connection including the hose-end temperature thermistor 108 at the point of delivery of heated air to the patient and the control circuit where the output of the sensing device is used to control the temperature of the heated air. Due to the difference in the heating levels upon switching between selected temperature ranges, the control unit will alter and delay the temperature alarm sensing to allow the temperatures to reach the nominal selected value.

The alarm circuit function may be activated by shorting the thermistor which represents a high temperature. Although a thermistor is the preferred sensor, other sensing devices may be used. The heater current is monitored by a sensing circuit, such as a secondary winding of a transformer, to monitor the heater current at all times. A variable speed blower motor may be utilized and can be calibrated so that the air speed can be controlled during manufacturing or maintenance to be consistent from unit to unit.

The control unit 202 of the preferred embodiment includes both analog and digital electronic components to implement the control and monitoring functions described herein. However, the control unit 202 is not limited to the specific embodiment detailed, and the present invention may be practiced by using a control unit with the performance features described, and independent from the specific technology used to implement any specific performance feature.

The control unit 202 has a power subsystem that provides power initialization, power on, and standby modes as well as providing a reference voltage for use throughout the measurement and control subsystem.

The control unit 202 has a self test subsystem that provides a self test sequencer that automatically proceeds through a temperature measurement thermistor open circuit test, a safety thermistor open circuit test, a heater open circuit test, a safety circuit test, and a lamp/alarm test upon power on condition as a part of a power on self test. At the completion of this power on self test, the control unit will reset to a state of providing ambient temperature air flow provided that no other temperature setting was selected during the power on self test.

Figure 4:
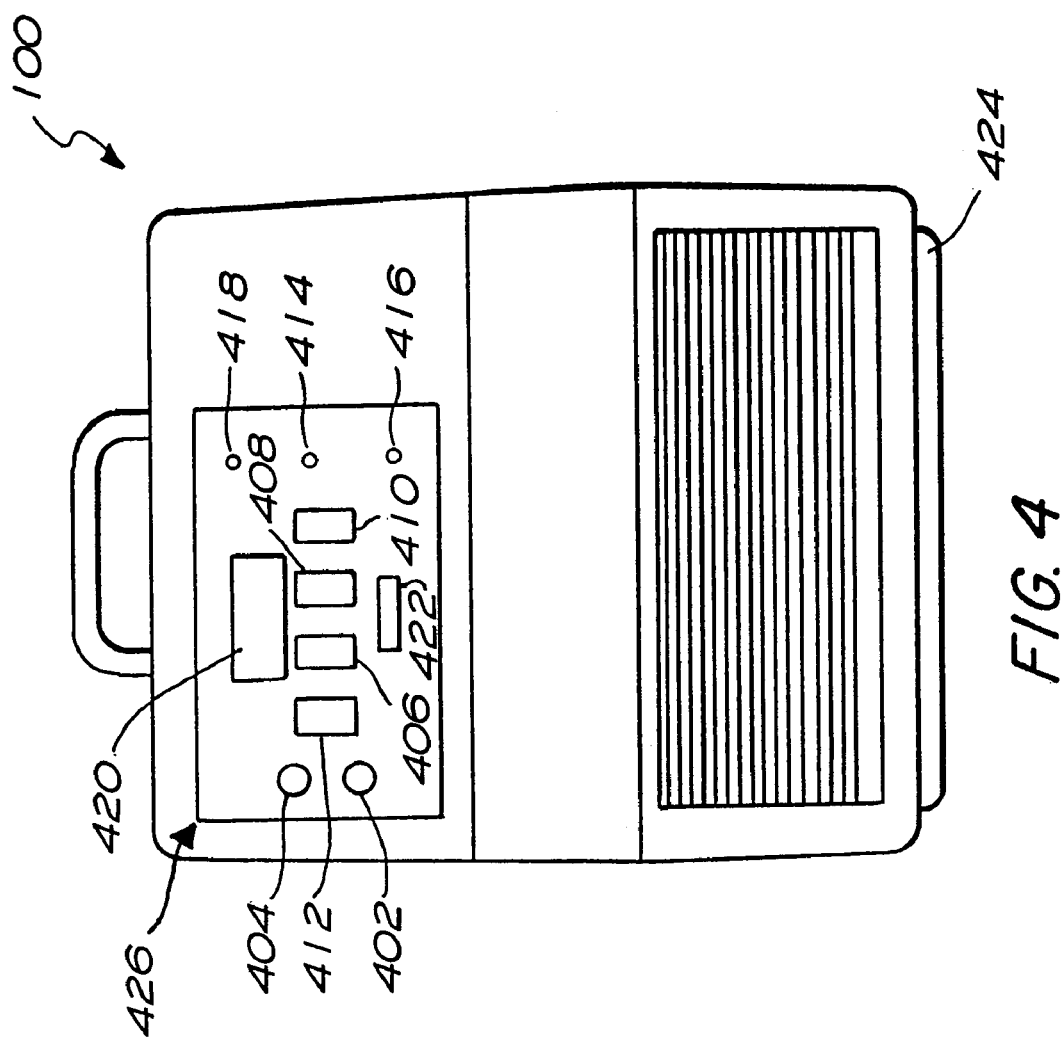
FIG. 4 shows a front panel of the warm air blower system with control switches and display indicators that comprise the user interface, or user Input/Output (I/O) interface.

As shown in FIG. 4, the power on condition is initiated by actuating the power on control switch 402. The power off condition is initiated by actuating the power off/standby control switch 404. An alarm condition can be reset by pressing the power off/standby control switch 404. After power on, and following self-test, the system is ready for temperature selection. Temperature selection is made by actuating the desired set temperature control switch: Low 406, Medium 408, or High 410, as shown in FIG. 4. Ambient un-heated air temperature is selected by switch 412 or automatically following the self-test, and may also be selected following the selection of another temperature setting.

The numerical value of the temperature of the delivered air from the warm air blower system is indicated to the user by display 420. The elapsed time in hours, indicating the total accumulated time the warm air blower system has been operating, is shown in the display 422. The elapsed time display 422 may be reset by holding the power on 402 and high temperature select 410 during the automatic self-test described infra. All of the user displays and controls may be generally considered as user I/O members 426. However, the elapsed time display reset is not considered a user I/O member since the user is never expected to reset the elapsed time display.

Actuating the low switch 406 will direct the warm air blower to provide heated air at 36° C. The medium switch 408 will direct the warm air blower to provide heated air at 40° C. The high switch 410 will direct the warm air blower to provide heated air at 44° C. The ambient switch 412 will direct the warm air blower to provide un-heated air at room temperature. A filter 424 may be attached, including a HEPA cartridge. The filter 424 can be placed in a first position to filter air before induction to the compression unit 208. Alternatively, the filter 424 can be placed in a second position to filter air after induction to the compression unit 208 and before the air is passed to the flexible conduit 102. In another alternative, two filters can be used to filter air in the first position and the second position so that air is filtered both before induction to the compression unit 208 and before being passed to the flexible conduit 102.

Should the control unit 202 fail to control the heater current, for example if the heater unit 206 is constantly energized and the hose-end temperature rises sufficiently above the set point, an over temperature safety unit 1608 will sense the runaway condition and cause the blower system to cease heating and air blowing.

When selecting a temperature that is lower than the previous temperature, a temperature down-step alarm delay to the alarm circuitry can be initiated to allow the warm air blower to respond properly to the newly set temperature. This delay can be typically between 60–90 seconds, although not limited to this range of values, and allows the temperature to change gradually from the higher temperature to the lower temperature before indicating an alarm condition. In addition to a visible alarm, an audible alarm can be emitted to indicate an over-temperature condition.

Conversely, for an under temperature condition, the UnderTemp indicator 414 will illuminate to indicate the hose-end temperature is more than 3° C. below the set temperature. The disconnect indicator 416 provides a visible indication if the air delivery hose is not properly attached to the cabinet of the air blower system.

The heater open circuit detector can function to detect the loss of current in the heater circuit and shut off the power to the heater and compression units and activate the disconnect indicator 416. This loss of current can be caused by a failure of the heater material itself, heater wiring, or the control unit. The current detection circuitry can use a transformer with a first winding in series with the current flow for the heater coils. A second winding provides an indication to the control circuitry regarding the current flow in the first winding.

The Manual over-temperature OverTemp Check Circuit can be initiated by persistently actuating any one of the set temperature controls (Low 406, Medium 408, High 410, Ambient 412) for an extended period, for example more than 8 seconds. This causes the control unit to energize the heater coils so that the temperature will rise until the delivered air temperature reaches the specified limit for the set temperature. When the upper limit is reached, the OverTemp monitoring circuit in the control unit can detect the over-temperature condition and cause the blower system to cease heating and air blowing, and initiate an OverTemp alarm condition by activating the OverTemp alarm indicator 418 and an audible alarm.

FIG. 2 shows an interior view of the warm air blower system showing the control unit 202, a plenum member 204 having a curvilinear interior surface, a heater unit 206, and a compression unit 208. In reference to FIG. 15, the control unit 202 includes the user I/O 426, the control unit circuit 1502, the hose connection sensor 110, and a hose-end temperature thermistor 108.

Figure 3:
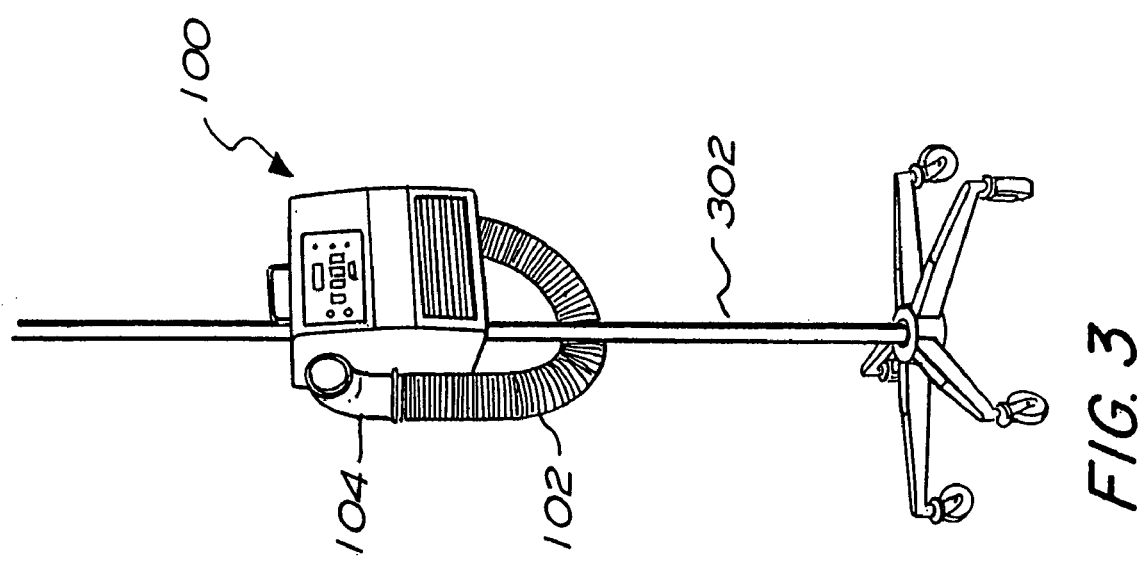
FIG. 3 shows a perspective view of the warm air blower system mounted on a support pole, such as a portable Intravenous (IV) pole.

FIG. 3 shows a perspective view of warm air blower system 100 mounted on a support pole 302, such as a portable IV pole or bed-mounted support in a hospital environment. Alternatively, the warm air blower system 100 can be mounted on a bed or a floor rolling cart. In another alternative, the warm air blower system 100 can be floor mounted.

Figure 5:
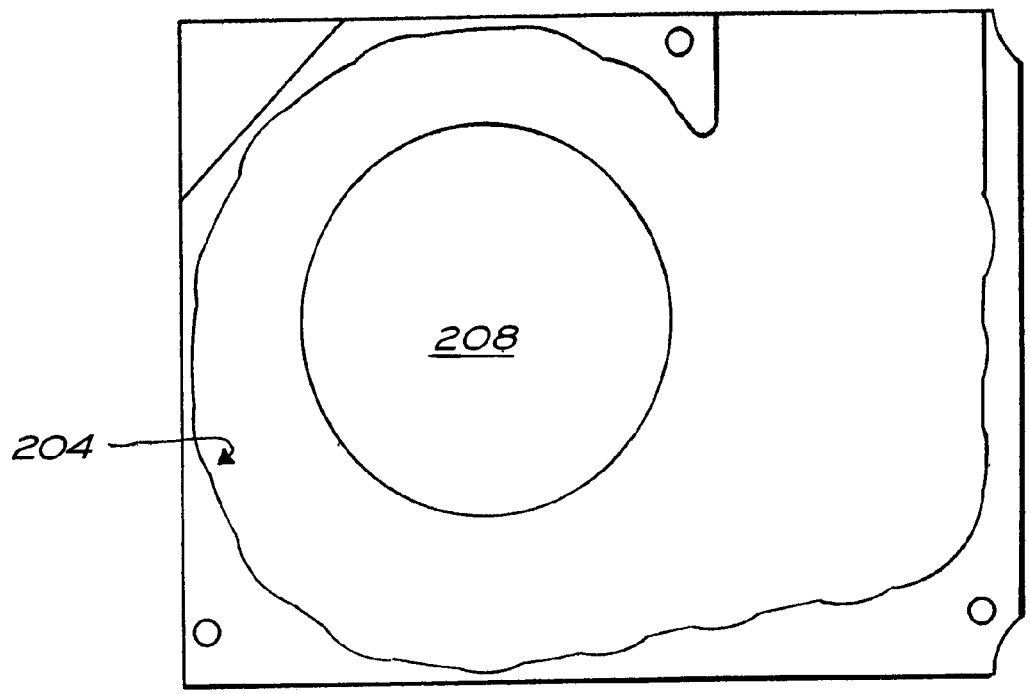
FIG. 5 shows a schematic top plan view of the plenum showing one example of a plenum chamber side wall with line-symmetric indentations.

FIG. 5 shows a schematic top plan view of the plenum with the plenum member 204 and the compression unit 208.

Figure 6:
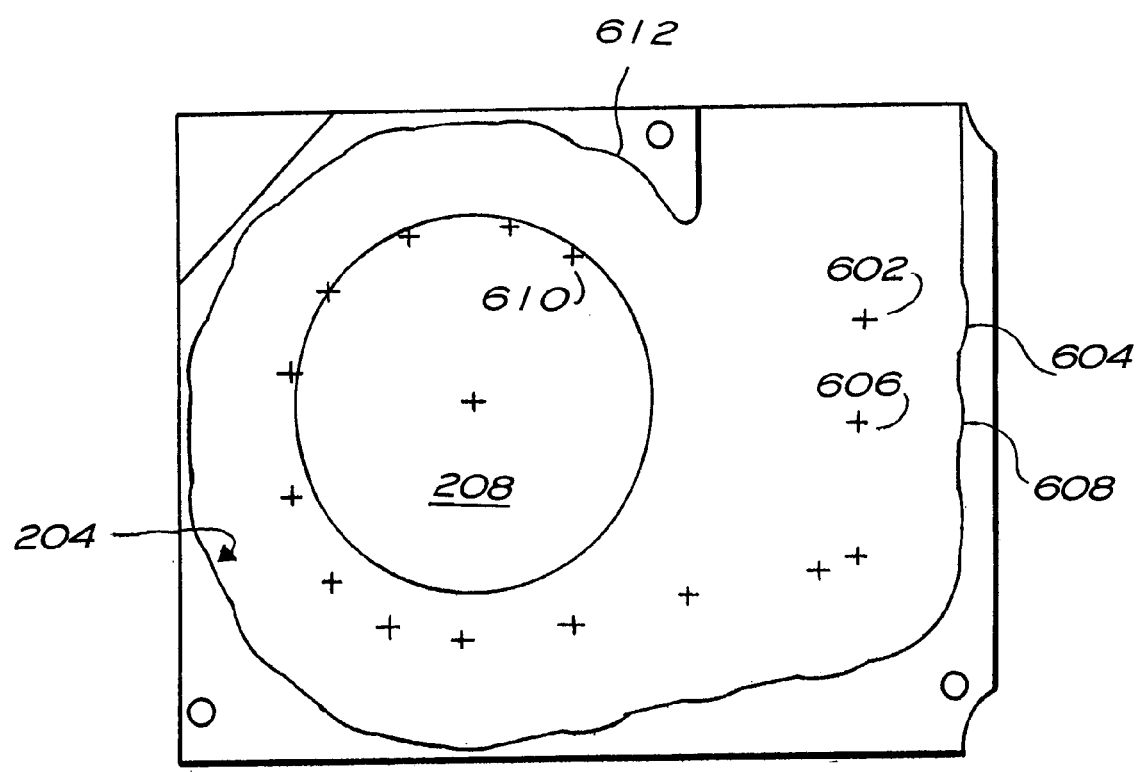
FIG. 6 shows an illustrative top plan view of the plenum of FIG. 5 with cross marks indicating the radii of curves imposed on the curvilinear internal plenum surface as one example of a plenum chamber side wall with line-symmetric indentations.

FIG. 6 shows an illustrative top plan view of the plenum with plus signs "+" or cross marks indicating the radii for the curves imposed on the interior surface of the plenum chamber that, in one embodiment, produces the line-symmetric or groove indentations on the interior surface. Some radii are shown (602, 604, 610) along with their corresponding line-symmetric indentations (604, 608, 612). The description and location of the particular indentations shown in this specification and the included drawings are not meant to be limiting, but rather illustrative. The location and depth of indentations may vary.

Figure 7:
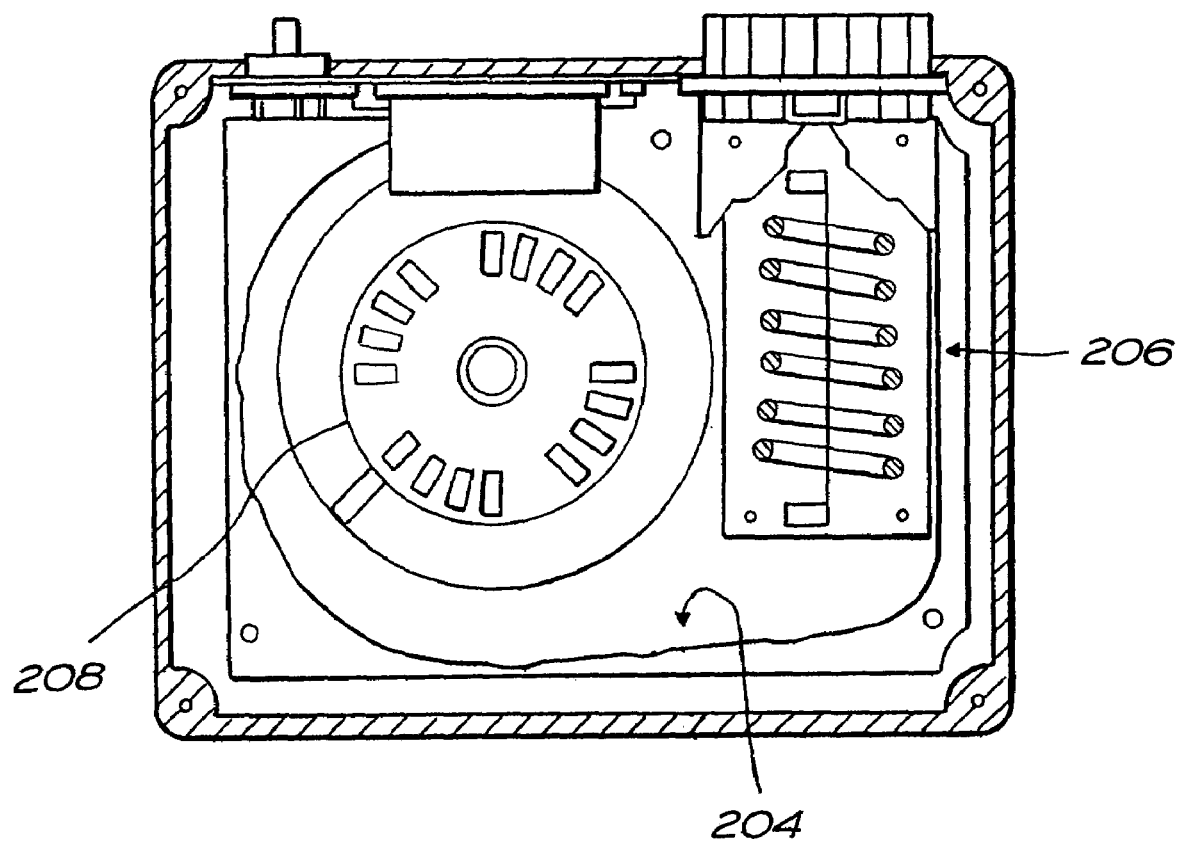
FIG. 7 shows a top plan cross sectional view of the plenum chamber with heater coils positioned in the plenum chamber and a cover plate taken off.
Figure 8B:
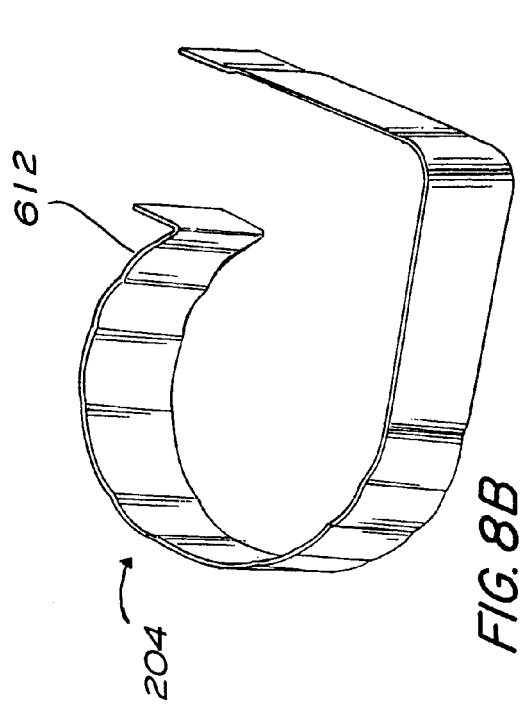
FIGS. 8A–8D show different views of one example of a plenum wall interior surface removed from the plenum chamber.
Figure 8D:
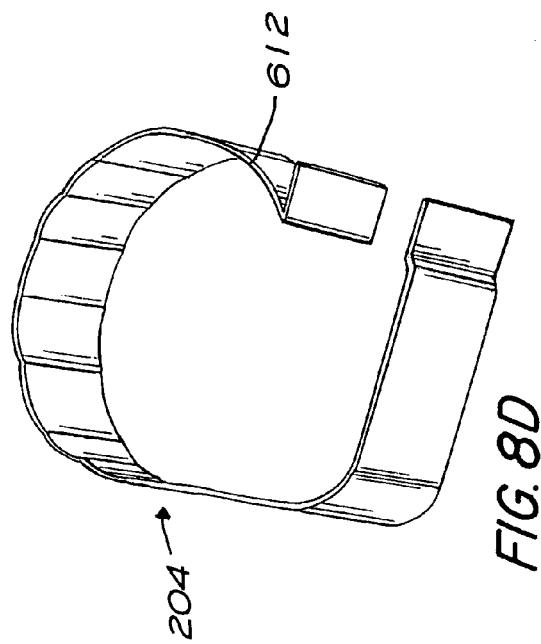
Figure 8A:
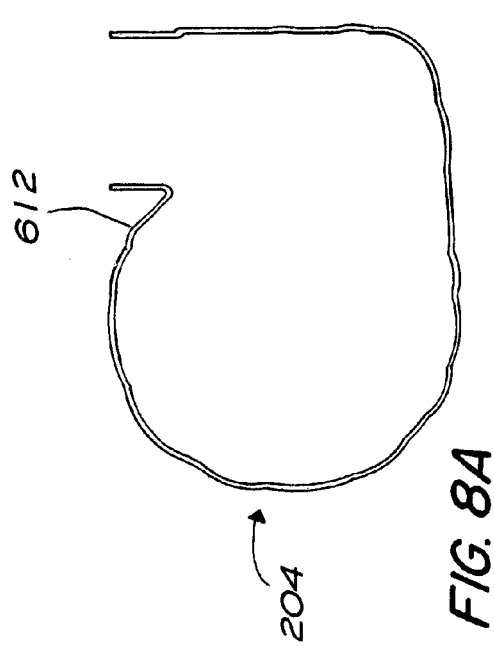
Figure 8C:
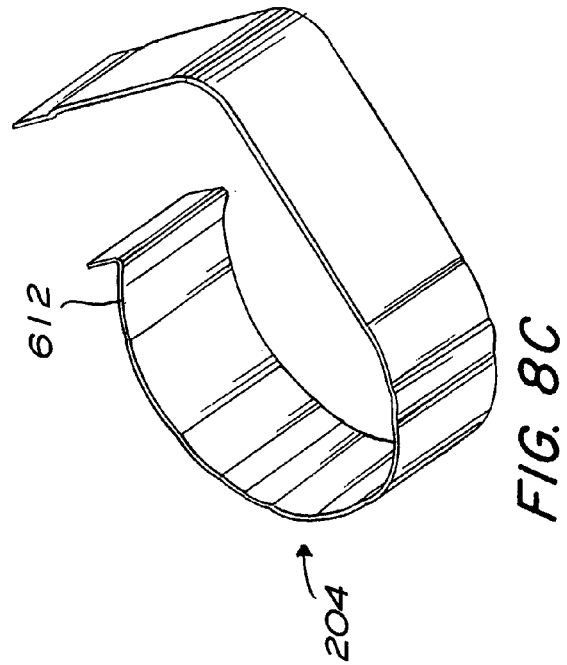

FIG. 7 is a top plan cross sectional view showing the plenum chamber with the plenum member 204 having a curvilinear interior surface, heater unit 206 including a heater coil, and the compression unit 208 positioned relative to the plenum chamber for a compact design.

According to the views of FIGS. 8A–8D, the plenum member 204 may be removed from the plenum chamber. This facilitates the manufacture of the plenum wall interior surface, for example out of a single piece of semi-rigid material. This semi-rigid material may be roll-pressed, for example, with any desired pattern of indentations, and then cut to fit the length of the plenum wall interior surface.

The single piece of semi-rigid material is then formed by any suitable process to fit the profile of the curvilinear interior surface of the plenum wall with the indentations adjacent to the interior of the plenum chamber. Alternatively, the removable plenum member 204 may be placed adjacent to a smooth plenum wall member as a laminar sheet so that the smooth plenum wall supports the plenum member 204 with the indentations adjacent to the interior of the plenum chamber. The plenum chamber may be fabricated as a single piece including a smooth plenum member wall, the plenum chamber then receives an indented plenum member as described herein to form a layered plenum wall interior surface.

Figure 9:
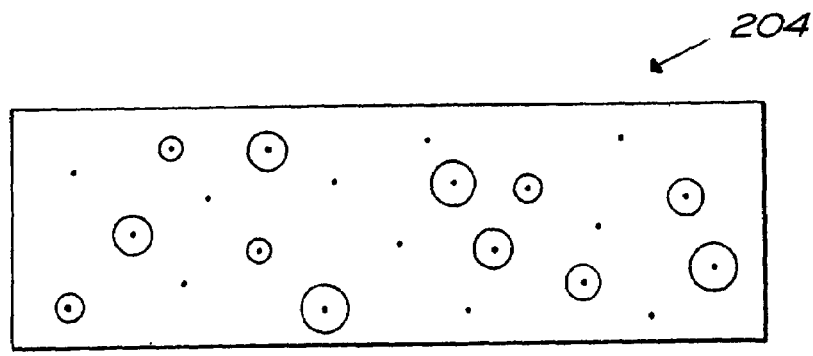
FIG. 9 shows a schematic indentation pattern for a plenum wall interior surface showing irregular point-symmetric indentations where the indentations vary both in location and depth but exhibit symmetry about a point.
Figure 10:
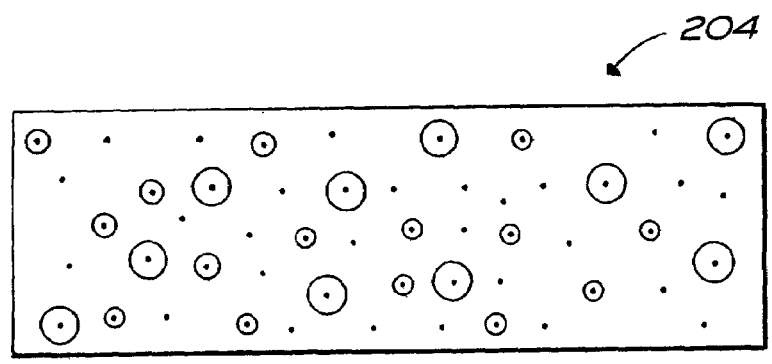
FIG. 10 shows another schematic indentation pattern with point-symmetric indentations.

FIGS. 9–10 illustrate a side view of a portion of the plenum wall interior surface showing another embodiment of the present invention using point-symmetric indentations. The indentations can be irregularly spaced and can have an irregular depth relative to neighboring indentations allowing the suppression of noise with harmonic vibration components.

Figure 11:
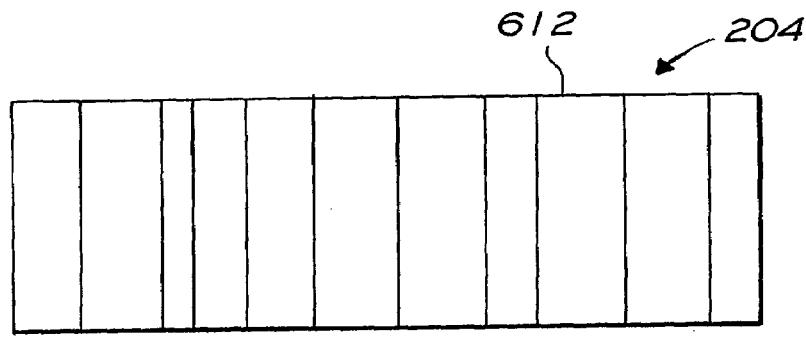
FIG. 11 shows a schematic indentation pattern for a plenum wall interior surface showing irregular line-symmetric indentations where the indentations vary both in location and depth but exhibit symmetry about a line.
Figure 12:
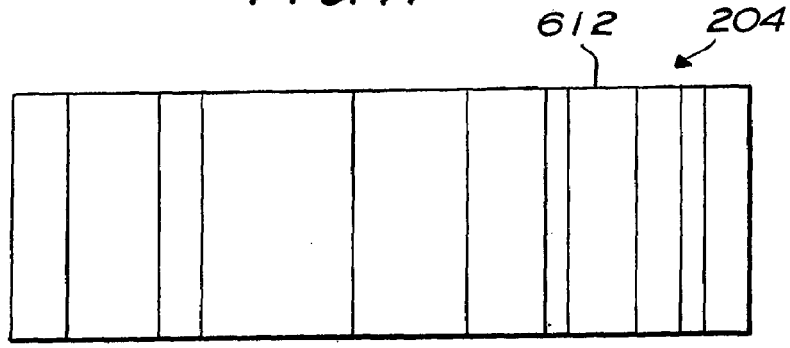
FIG. 12 shows another schematic indentation pattern with line-symmetric indentations.

FIGS. 11–12 illustrate a side view of a portion of the plenum wall interior surface showing another embodiment of the present invention using line-symmetric indentations. For example, one line-symmetric indentation 612 is shown. The indentations are irregularly spaced and have an irregular depth relative to neighboring indentations allowing the suppression of noise with harmonic vibration components.

The plurality of surface indentations enable the formation of controlled local turbulence adjacent the interior surface to reduce friction and noise as compressed air moves across the interior surface.

Figure 14:
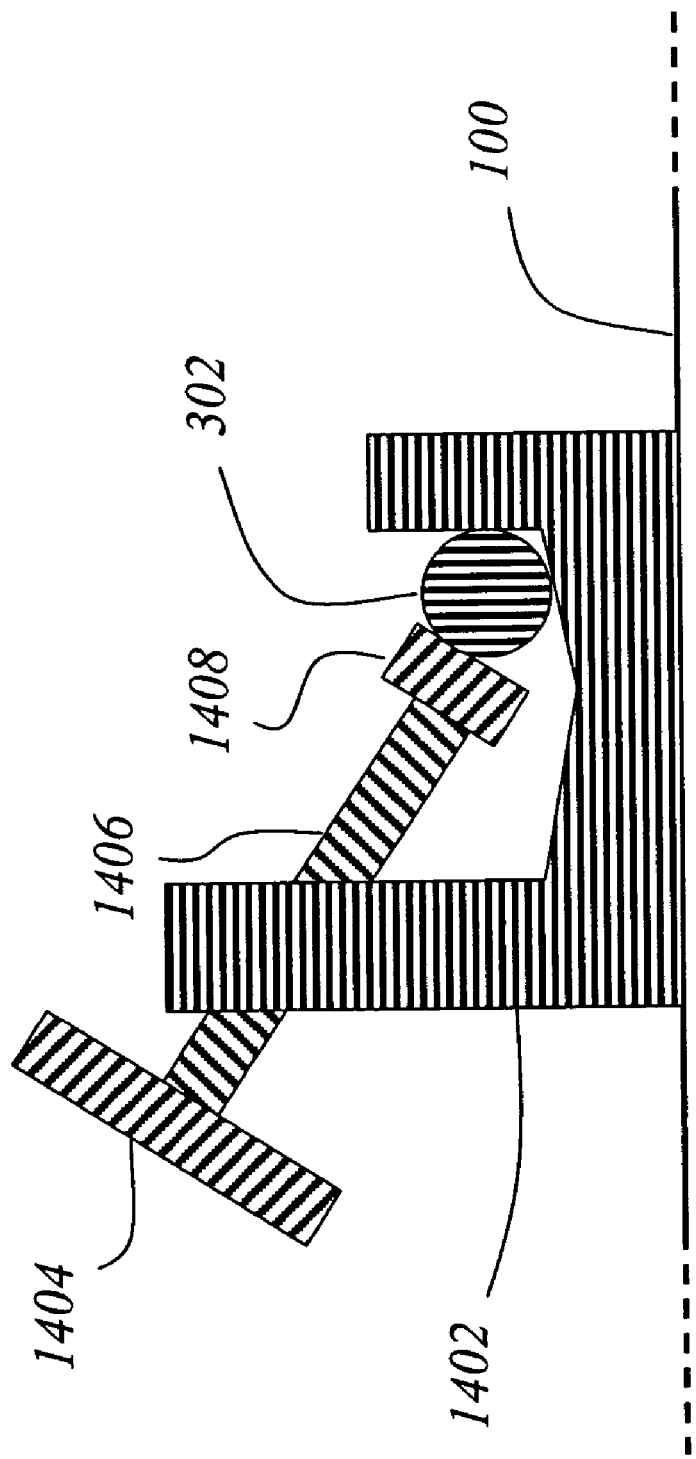
FIG. 14 shows a mounting apparatus for releasably mounting the blower system to a mounting member like a portable intravenous fluid holding pole (IV pole).

FIG. 14 shows the mounting apparatus 1402 for releasably mounting the warm air blower system 100 to a mounting member 302 like a portable intravenous (IV) fluid holding pole, or IV pole. The mounting apparatus 1402 is attached to the rear of the warm air blower system 100 and allows the warm air blower system to be mounted off the floor, and within easy reach of an operator. The mounting apparatus 1402 has a screw head 1404 for turning a screw 1406 threaded through a portion of the mounting apparatus 1402 and carrying a friction bumper 1408 against a mounting member 302, such as an IV pole, so that the mounting member is held securely in the mounting apparatus and the warm air blower system 100 is supported by attachment to the mounting member 302.

The screw 1406 is turned in one direction to tighten the friction bumper 1408 against the mounting member 302 and turned in the other direction to loosen the friction bumper 1408 from the mounting member 302 and allow release from the mounting member 302. The components of the mounting apparatus 1402 and the mounting member 302 may have a different shape than that disclosed in the drawings as long as the function of releasably attaching and supporting the warm air blower system to a mounting member is fulfilled.

DESCRIPTION OF CONTROL UNIT

Figure 15:
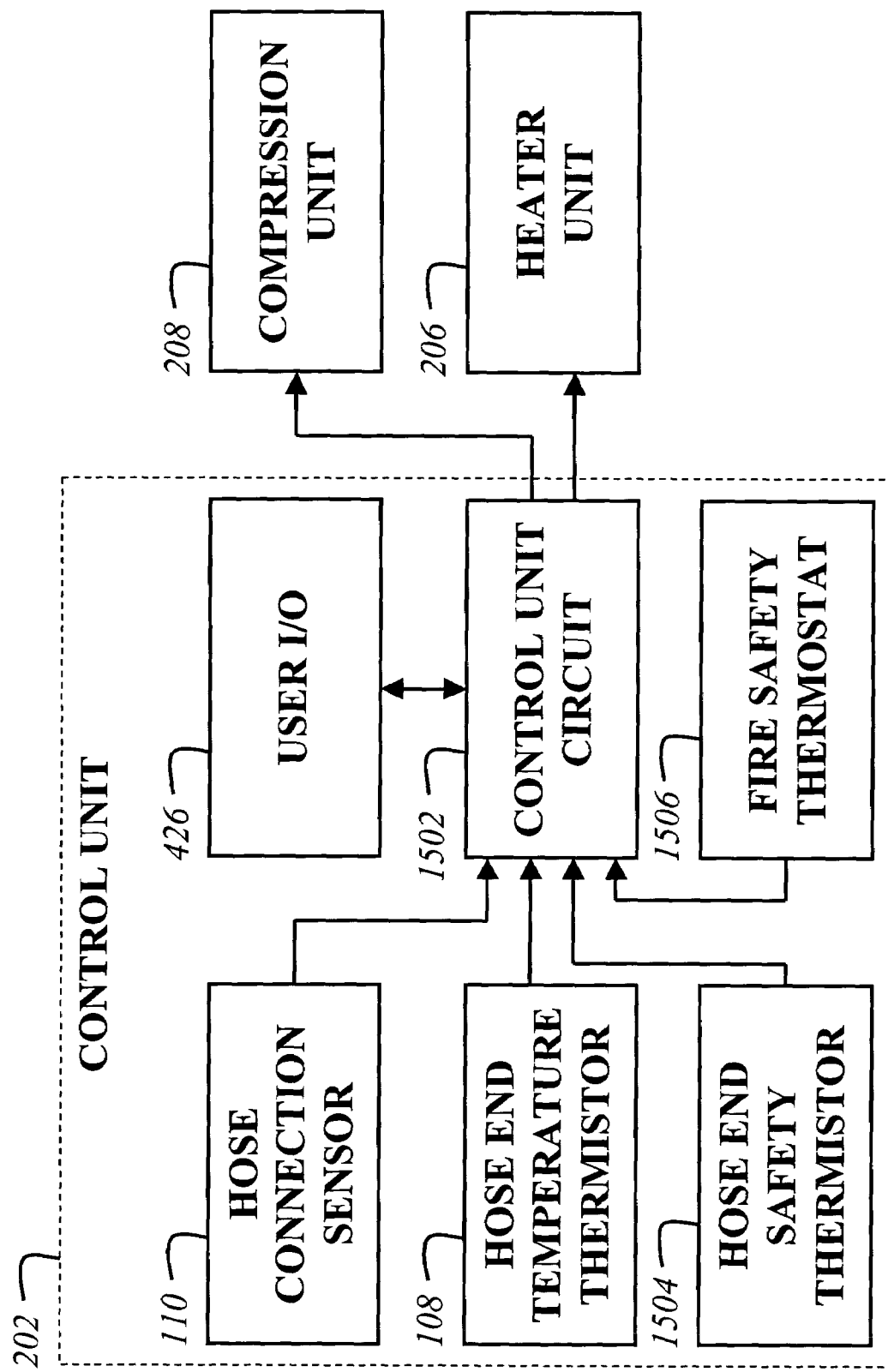
FIG. 15 shows a top-level block diagram of the control unit including the compression unit and the heater unit.

FIG. 15 shows a block diagram of the control unit 202. The control unit 202 includes a user input/output (I/O) block 426, a control unit circuit 1502, a hose connection sensor 110, a hose-end safety thermistor 1504, a hose-end temperature thermistor 108, and a fire safety thermostat 1506. The control unit 202 elements cooperate to drive the compression unit 208 and the heater unit 206. The compression unit 208 can be a fan and motor assembly comprising a blower motor.

Figure 16:
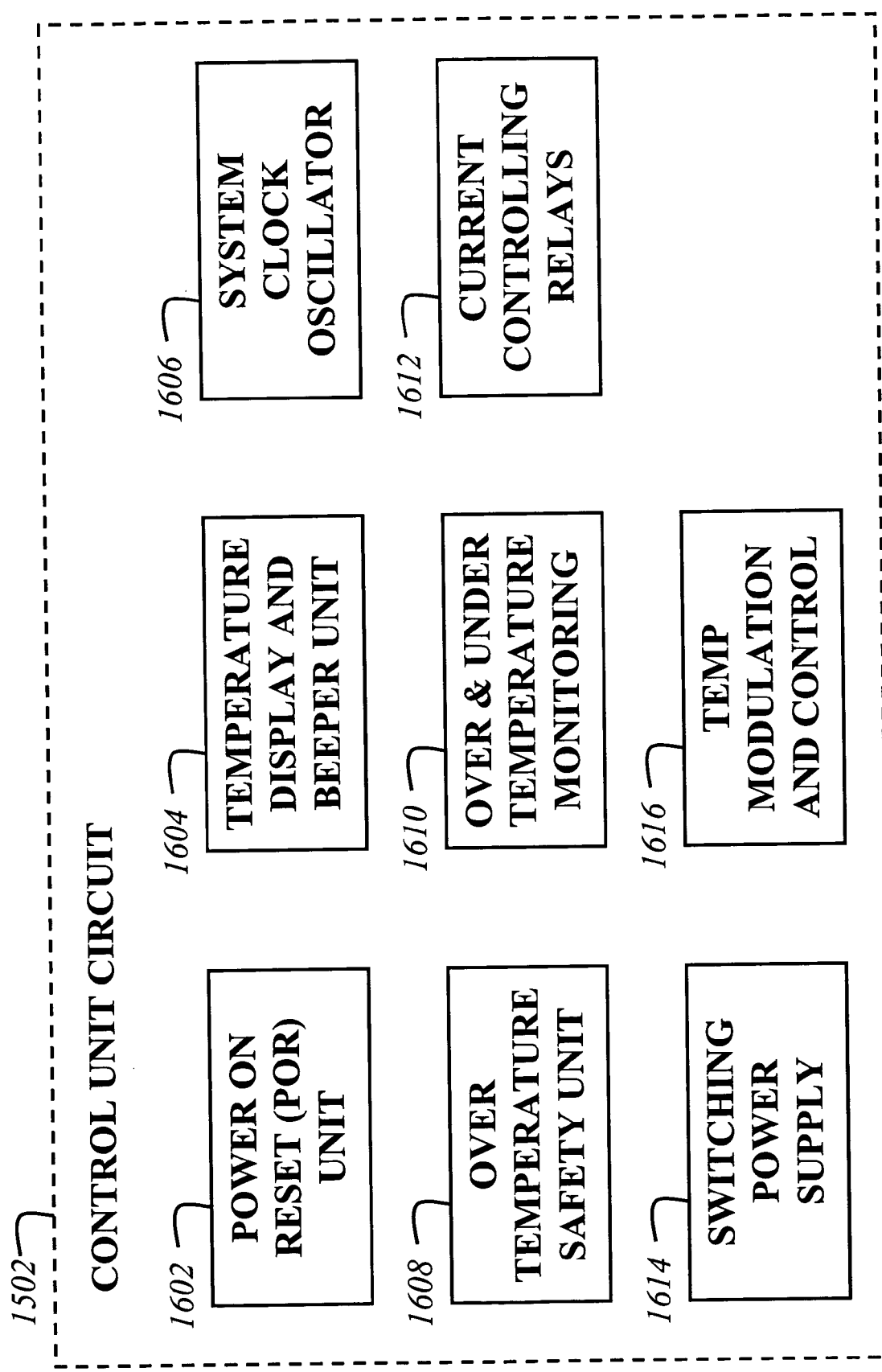
FIG. 16 shows a top-level block diagram of some elements of the control unit circuit.

FIG. 16 shows some of the components of the control unit circuit 1502, including a power on reset (POR) unit 1602, a temperature display and beeper unit 1604, a system clock oscillator 1606, an over-temperature safety unit 1608, an over and under temperature monitoring circuit 1610, current controlling relays 1612, a switching power supply 1614, and a temperature modulation and control circuit 1616. The system clock oscillator 1606 provides timing synchronization throughout the control unit circuit 1502.

Figure 17:
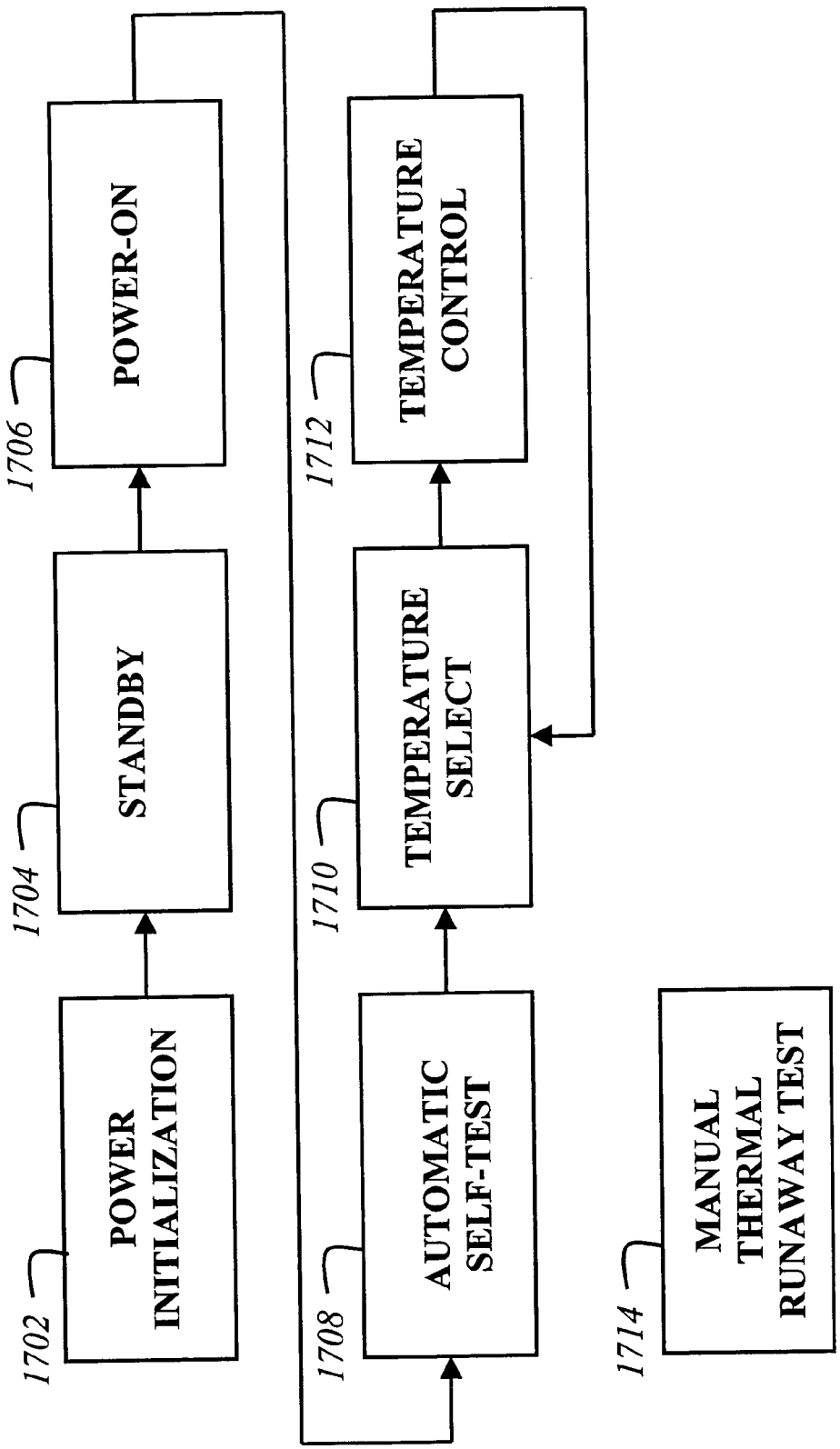
FIG. 17 shows the control unit modes of operation.

FIG. 17 shows the control unit 202 modes of operation and can include a sequence of operations where one mode leads to another mode. The control unit modes include a power initialization mode 1702, a standby mode 1704, a power-on mode 1706, an automatic self-test mode 1708, a temperature select mode 1710, a temperature control mode 1712, and a manual thermal runaway test mode 1714.

The power initialization mode 1702 occurs when line power is applied to the control unit 202. The line power then supplies a switching power supply through a line fuse and the rest of the circuit through a fire safety thermostat 1506. A mechanical relay supplies line power to both the compression unit motor and the heater through the thermostat. If the mechanical relay or thermostat is open, neither the compression unit nor the heater unit will be supplied with power.

A current sensing transformer can be in the heater return line to the mechanical relay. A second relay opens the neutral to the heater if the hose becomes disconnected as indicated by hose connection sensor 110 that senses whether there is a hose connection to the air outlet. The compression unit 208 motor can be protected by a fuse.

In reference to FIGS. 16–17, the switching power supply 1614 provides 5 Vdc to a printed circuit board (PCB) that can contain the control logic elements of the control unit circuit 1502. When the 5 Vdc power is established, a power on reset (POR) is asserted that resets the control unit to standby (STDBY) mode 1704.

In reference to FIG. 4, pressing the ON switch 402 terminates all standby conditions and causes the control unit 202 to enter the power-on mode 1706 shown in FIG. 17. In the power-on mode 1706, the control unit 202 initiates an automatic self-test 1708 and then enables the ambient (AMB) temperature selection mode 1902 shown in FIG. 19. This enables the mains power relay that activates the compression unit 208 motor.

In reference to FIG. 4, pressing the Power-OFF/STDBY button 404 resets the control unit 202 to standby mode 1704. This opens the current flow to the mains power relay, control relay, and to the alarm indicators. It also cancels a self-test in progress.

In reference to FIG. 4, after the power-on 1706 mode is completed, the automatic self-test 1708 can be initiated. In reference to FIG. 18, the automatic self-test 1708 includes a temperature thermistor disconnect test 1802, a safety thermistor disconnect test 1804, a heater current test 1806, a safety circuit test 1808, and an alarm/lamp test 1810.

Figure 18:
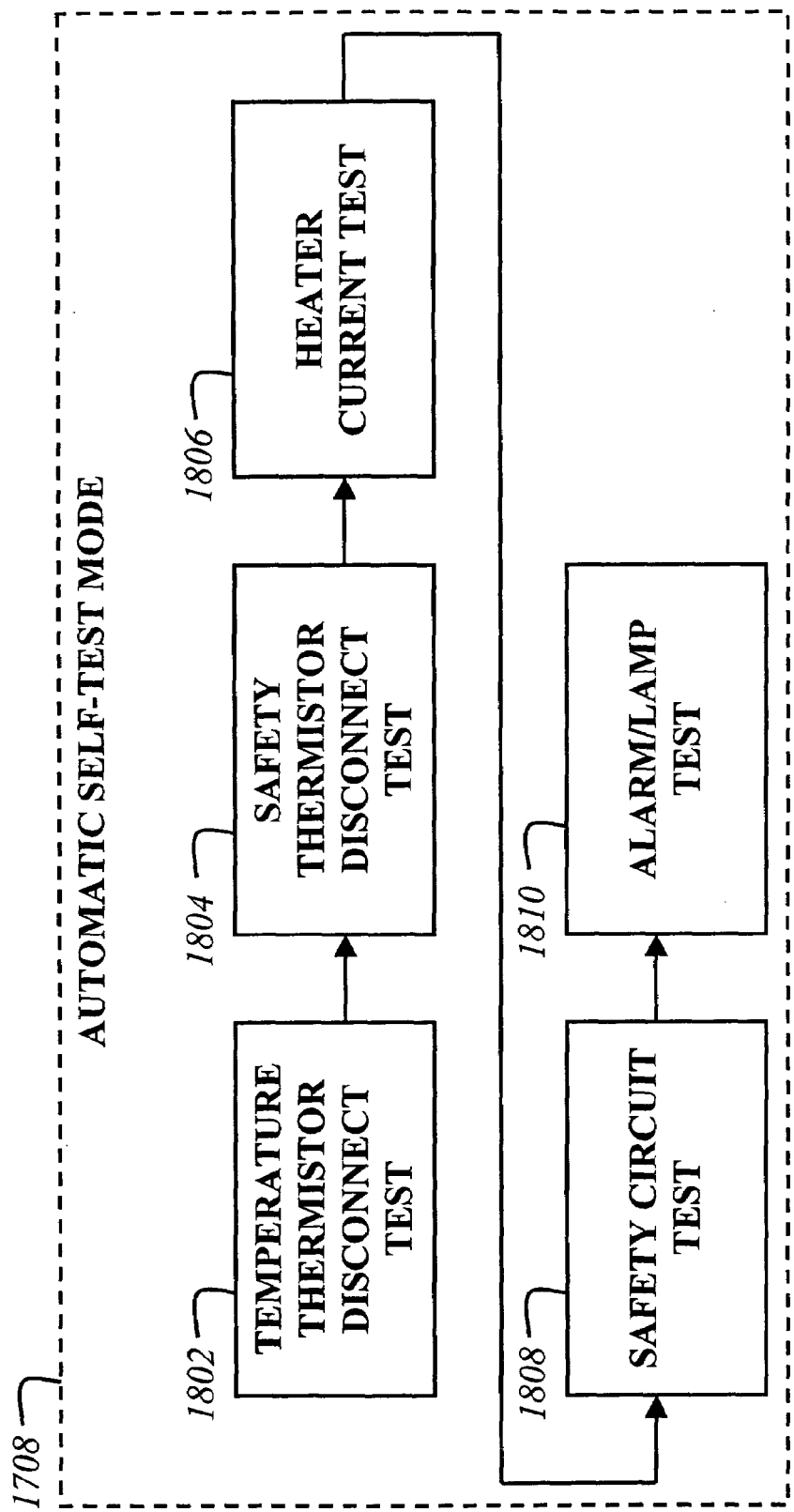
FIG. 18 shows the automatic self-test mode of the control unit modes of operation.

In reference to FIG. 18, the automatic self-test 1708 starts with the temperature thermistor disconnect test 1802. This test can cause the thermistor output to be grounded which has the same effect as the temperature measurement thermistor being a high impedance or open circuit to test the sensing comparator. This condition can turn on the disconnect indicator LED 416 for visual indication of the problem condition.

The Hose Disconnect sensor 110 has the same effect on this self-test mode thereby testing whether the flexible conduit 102 is improperly inserted into the warm air blower system 100. If the flexible conduit 102 is not sufficiently inserted into the air outlet to hold the hose connection sensor 110 switch in an actuated (closed) position, this mode of the self-test will stop here indicating the problem condition. Similarly, this condition can turn on the disconnect indicator LED 416 for visual indication of the problem condition.

In reference to FIG. 18, after completing the temperature thermistor disconnect test 1802, the automatic test 1708 can proceed to the safety thermistor disconnect test 1804. This can have the same effect as the safety thermistor being a high impedance or open circuit to test the sensing comparator. This turns on the disconnect indicator LED 416 for visual indication of the problem condition.

After completing the safety thermistor disconnect test 1804, the automatic testing proceeds to the heater current test 1806. The self-test can then simulate a request for heat while the current path to the heater element is open. This, along with the fact that there is (or should be) no heater current, creates a disconnect condition. This condition turns on the disconnect indicator LED 416 for visual verification of operation. If there is an indication of heater current in this test, it should fail and stop at this point.

After completing the heater current test 1806, the automatic testing proceeds to the safety circuit test 1808. The safety circuit test 1808 creates an alarm condition at the sensing input to verify the proper operation of disabling the mains relay, disabling the heater, causing an alarm beeper to emit a short audible sound for audible verification of operation and illuminating the visual OverTemp indicator for visual verification of operation.

During the self-test 1708, the AMB, LO, MED, HI and UT LEDs illuminate for visual verification of operation. The lamp test 1810 operates concurrently with the self-test.

In reference to FIG. 16, the control unit circuit 1502 includes a system clock oscillator 1606 that is a free-running 2 KHz oscillator generated by a standard complementary metal oxide semiconductor (CMOS) resistive-capacitive (RC) oscillator including components. The actual value of the clock frequency depends upon the specific values of the components selected, and is not critical. Within normal component tolerances, the referenced frequency is between 1.6–2.2 KHz. The referenced frequencies and time durations within this specification are calculated based on an exact 2 KHz clock frequency and can vary accordingly.

In reference to FIG. 17, following the automatic self-test, the temperature selection mode (AMB, LOW, MED, HIGH) is entered. In reference to FIG. 19, if the operator pressed a temperature select button following power on, the selected setting (1904, 1906, 1908) can be entered following the self-test. However, if the operator has not entered a temperature selection, then the ambient temperature mode 1902 is entered by default.

Figure 19:
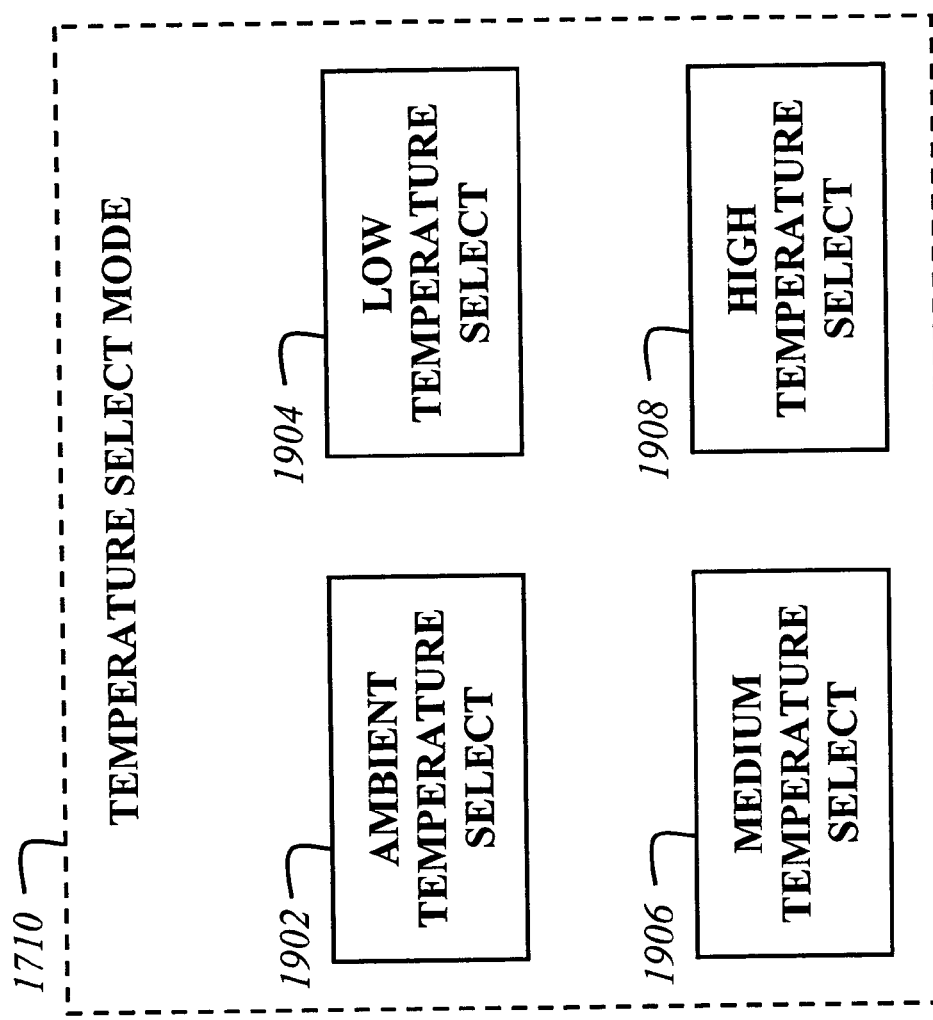
FIG. 19 shows the temperature select mode of the control unit modes of operation.
Figure 20:
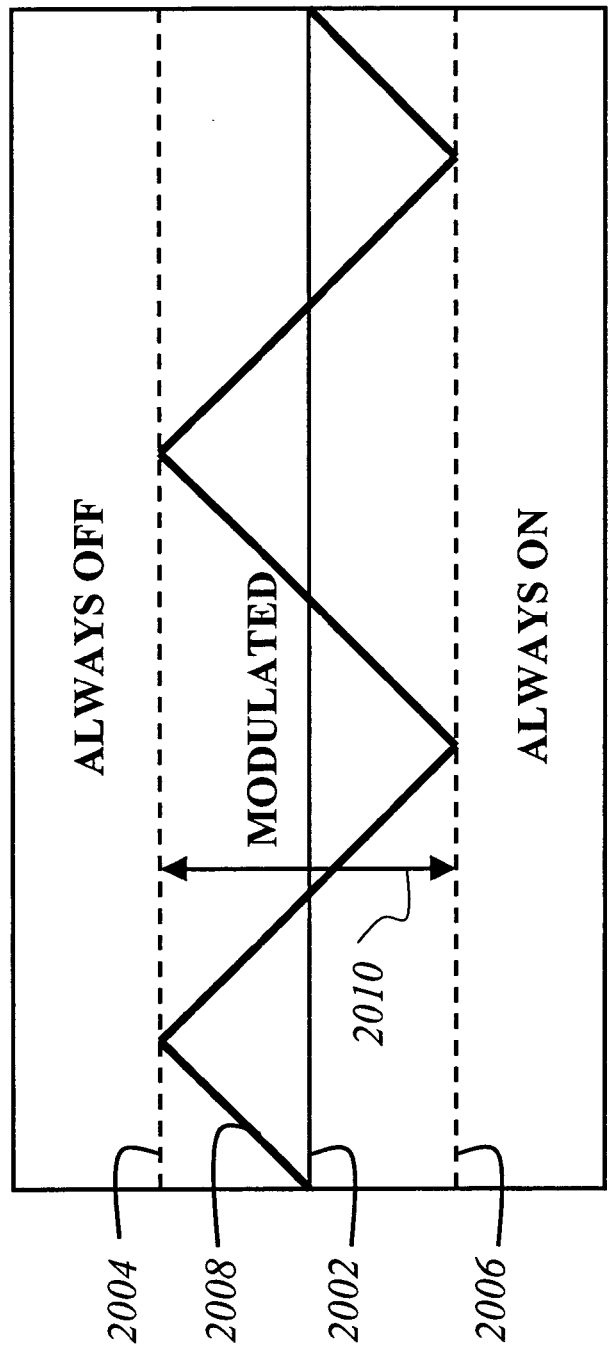
FIG. 20 shows a timing chart for a temperature control mode of the control unit modes of operation showing the temperature can be maintained by modulating the current to the heater unit.

In reference to FIG. 17, once a temperature has been selected in the temperature select 1710 mode, the selected temperature is maintained in the temperature control mode 1712. The temperature can be maintained by modulating the current to the heater unit 206 as shown in FIG. 20. The set temperature is selected in the temperature select mode 1710 to be Ambient 1902, Low 1904, Medium 1906, or High 1908, as shown in FIG. 19.

The set temperature is the target temperature the control unit 202 is seeking to maintain. As shown in FIG. 20, if the difference between the hose-end temperature and the set temperature is at or below the lower limit 2006, the current to the heater unit 206 will be always on. Conversely, if the temperature differential is at or above the upper limit 2004, the current to the heater unit 206 will be always off.

The actual temperature differential 2002 is compared against the free running oscillator generated triangle wave modulating the current to the heater unit 206 in order to remain in the range 2010. If a lower temperature is then selected from the user interface, the current to the heater unit 206 is always off until the differential temperature is within the modulated heat area again.

In reference to FIG. 16, should the temperature modulation and control circuit 1616 fail to control the heater current in such a way that the heater is constantly on or the hose-end temperature rises sufficiently above the set point as indicated by the hose-end safety thermistor 1504, the over temperature safety circuit 1610 can sense the runaway condition and stop the current flow to the heater unit 206 and the compression unit 208.

The user display 420 can hold the temperature detected that has caused the problem condition and can indicate an over temperature alarm by illuminating the over temperature indicator 418 and emitting a sound from the beeper element (not shown) driven by the temperature display and beeper unit 1604. Internally, the control unit circuit 1502 can redundantly disable the current path to the heater unit for added safety. When an over temperature problem condition is detected, the OverTemp indicator 418 will illuminate and an audible alarm will sound.

If selecting a new set temperature that is lower than the previous set temperature, such as from High 1908 to Low 1904, an immediate alarm condition may ordinarily be falsely be created because the hose-end safety thermistor is above the new Low 1904 over-temperature setting value. To avoid this false alarm the alarm condition is altered for a period of time by a redundant delay counter pair after the down-step in temperature.

Similarly, if the operator is starting at High 1908 and then down selecting to Medium 1906 and then down selecting to Low 1904 or Ambient 1902, the alarm condition delay counter can restart the counters at the beginning of each selection. Over temperature alarm preset temperatures are the selected temperature plus 3° C. or 47° C. for Ambient. An alarm condition can be reset by pressing the power off (STDBY) button 404. This creates a master reset of all the control circuit elements in the control unit circuit 1502.

In reference to FIG. 4, the under temperature (UnderTemp) indicator 414 functions to alert the operator that the hose-end temperature is approximately three or more degrees below the set temperature. In reference to FIG. 16, the over and under temperature monitoring circuit 1610 functions by testing the hose-end safety thermistor 1504 and comparing against a pre-set value for each temperature. When an under temperature problem condition is detected, the UnderTemp indicator 414 will flash slowly at approximately 0.5 Hz.

In reference to FIG. 4, the disconnect indicator 416 functions to show the disconnection or open circuit of the hose connection sensor 110, the integrity of either or both thermistor(s) or wires or the hose air inlet disconnection from the warm air blower system 100. Another function of the disconnect indicator 416 is to show when there is a problem in the heater circuit which was explained supra.

In reference to FIG. 17, initiation of the manual thermal runaway test can be accomplished by simply pressing and holding any of the temperature select buttons for approximately 8 seconds until the selection indicator on that button starts to flash at approximately 2 Hz. During this test, the heater unit 206 is turned fully on as discussed in reference to FIG. 20 regarding the modulation of the heater current. When the temperature rises above the OverTemp threshold for that temperature selection, the OverTemp Safety Circuit 1608 takes over. Pressing the STDBY button 404 resets control unit circuit 1502.

DESCRIPTION OF TESTS AND RESULTS

FIG. 13 illustrates the result of tests that were conducted to demonstrate the noise reducing benefits of the present invention by comparing the noise output of a Model EQ5000 Convective Warmer with a Model SW4000 Convective Warmer from Level 1, Inc. 160 Weymouth Street Rockland, Mass. 02370. The Model EQ5000 incorporates the noise reducing features of the present invention while the Model SW4000 does not include the noise reducing features. The noise was measured at the front of each unit.

The test procedure for each Convective Warmer unit was:
Connect the Convective Warmer unit to a Model SW2004 Convective Warmer Blanket using a 5-foot long hose. The Model SW2004 Blanket used in these tests is also available from Level 1, Inc.

Start the Convective Warmer unit and set to High Temperature 44° C. Allow the Convective Warmer to reach the proper temperature.

Measure the noise level (decibel/dB) at the front of each unit and record. For the Model EQ5000 adjust the air velocity from 1600 feet/minute to 2100 feet/minute in 50 feet/minute increments and repeat. The Model SW4000 was only tested at a constant air velocity of 2040 feet/minute. The air velocity can naturally fluctuate at +/−200 feet/minute.

FIG. 13 shows the recorded noise levels at the front of the warm air blower system of the present invention compared with a similar warm air blower system without the sound reducing features of the present invention. The Model EQ5000 noise level measured from 66.1 dB to 70.0 dB over the range of air velocity tested while the Model SW4000 noise level was measured at 71.8 dB for the air velocity of 2040 feet/minute.

The results show less audible noise levels at the front of the Convective Warmer unit that includes the noise reducing features of the present invention when compared with a Convective Warmer that does not include the noise reducing features of the present invention.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:
1. An air blower system comprising:
 a compression limit for compressing and directing air flow; and
 a plenum chamber operatively connected to the compression unit, the plenum chamber having a plenum member forming an interior wall with a curvilinear interior surface, the plenum member curvilinear interior surface having a plurality of predetermined surface indentations to enable the formation of a predetermined amount of controlled local turbulence adjacent the curvilinear interior surface to reduce friction and suppressed noise as the compressed air move across the curvilinear interior surface,
 wherein the plenum member curvilinear interior surface indentations are irregular and vary in depth to reduce fiction and suppress noise having harmonic vibration components.
2. The air blower system of claim 1, further comprising:
 an air filter, the air filter suitably positioned to filter air one of before and after induction to the compression unit.
3. The air blower system of claim 1,
 wherein the plenum member in removable from the plenum chamber, the removable plenum member being formed in one piece from a semi-rigid material.
4. The air blower system of claim 1,
 wherein the plenum member is formed as an irremovable part of the plenum chamber.
5. The air blower system of claim 1,
 wherein the plenum member curvilinear interior surface indentation are irregularly spaced.

6. A warm air blower system, comprising:
a compression unit, for compression and directing air flow;
a plenum chamber operatively connected to the compression unit, the plenum chamber having a plenum member forming an interior wall with a curvilinear interior surface, the plenum member curvilinear interior surface having a plurality of predetermined surface indentations to enable the formation of a predetermined amount of controlled local turbulence adjacent the curvilinear interior surface to reduce friction and suppress noise as the compressed air moves across the curvilinear interior surface;
a heater unit for heating the directed air;
a temperature tensor for measuring the temperature of the heated air the temperature sensor being located in close proximity to where the heated air is supplied to a cooperative receiving unit, and
a control unit to control and monitor the temperature of the heated are the control unit allowing the selection of a predetermined set temperature of the heated of the heated are;
wherein the predetermined set temperature is selected from a group consisting of 36° C.; 40°C.; and 4420 C.; the actual temperature of the heated air varying by ±1° C. from the selected set temperature, and
the control unit is capable of testing the operability of the warm air blower system, the control unit being responsive to a heated air over-temperature condition and a heated air under-temperature condition.

7. The warm air blower system of claim 6, further comprising:
an air filter, the air filter suitably positioned to filter air one of before and after induction to the compression unit.

8. The warm air blower system of claim 6,
wherein the plenum member is removable from the plenum chamber, the removable plenum member being formed in one piece from a semi-rigid material.

9. The warm air blower system of claim 6,
wherein the plenum member is formed as an irremovable part of the plenum chamber.

10. The warm air blower system of claim 6, further comprising:
a mounting apparatus for releasably mounting the warm air blower system to a mounting member.

11. The warm air blower system of claim 10,
wherein the mounting member is a support pole, a bed, or a floor rolling cart.

12. The warm air blower system of claim 6,
wherein the plenum member curvilinear interior surface indentations are irregular to reduce friction and suppress noise with harmonic vibration components.

13. The warm air blower system of claim 12,
wherein the plenum member curvilinear interior surface indentations vary in depth.

14. The warm air blower system of claim 6,
wherein the plenum member curvilinear interior surface indentations are irregularly spaced.

15. The warm air blower system of claim 6,
wherein the control unit allows a selection of ambient temperature so that unheated air is delivered by the warm air blower system.

16. The warm air blower system of claim 6,
wherein the control unit has a heated air over-temperature safety limit of 3° C. above the set temperature, the control unit detecting the over-temperature safety limit has been reached causes the warm air blower system to cease heating and air blowing, the control unit providing one or more indications of the heated air over-temperature condition, the indications being audible and visible.

17. The warm air blower system of claim 16,
wherein the control unit has a manually operated heated air over-temperature test mechanism where by the heater unit is energized to exceed the selected set temperature, the heated air temperature gradually increasing unit the heated air over-temperature safety limit for the predetermined set temperature is reached, the control unit responding to the over temperature condition by ceasing heating and blowing thereby verifying the proper operation of the control unit safety systems.

18. A warm air blower system, comprising:
a compression unit for compressing and directing air flow;
a plenum chamber operatively connected to the compression unit, the plenum chamber having a plenum member forming an interior wall with a curvilinear interior surface, the plenum member curvilinear interior surface having a plurality of predetermined surface indentations to enable the formation of a predetermined amount of controlled local turbulence adjacent the curvilinear interior surface to reduce friction and suppress noise as the compressed air moves across the curvilinear interior surface;
a heater unit for heating the directed air;
a temperature sensor for measuring the temperature of the heated air the temperature sensor being located in close proximity to where the heated air is supplied to a cooperative receiving unit; and
a control unit to control and monitor the temperature of the heated air, the control unit allowing the selection of a predetermined set temperature of the heated air, the control unit capable of automatically testing the operability of the warm air blower system, the control unit being responsive to a heated air over-temperature condition, and the control unit being responsive to a heated air under-temperature condition,
wherein the control unit provides a manually operated heated air over-temperature test to verify the proper response of the control unit to a heated air over-temperature condition, the control unit detecting when the over-temperature safety limit has been reached to cause the warm air blower system to cease heating and air blowing, the control unit providing one or more indications of the heated air over-temperature condition, the indications being audible and visible.

19. The warm air blower system of claim 18,
wherein the manually operated heated air over-temperature test has a upper temperature unit that is based on the predetermined set temperature selected by the operator.

20. An air blower system, comprising:
a compression unit for compressing and directing air flow; and
a plenum chamber operatively connected to the compression unit, the plenum chamber having a plenum member forming an interior wall with a curvilinear interior surface, the plenum member curvilinear interior surface having a plurality of predetermined surface indentations to enable the formation of a predetermined amount of controlled local turbulence adjacent the curvilinear interior surface to reduce friction and suppress noise as the compressed air moves across the curvilinear interior surface, wherein the plenum member is removable from the plenum chamber, the removable plenum member being formed in one piece from a semi-rigid material.

21. An air blower system, comprising:

a compression unit for compressing and directing air flow; and a plenum chamber operatively connected to the compression unit, the plenum chamber having a plenum member forming an interior wall with a curvilinear interior surface, the plenum member curvilinear interior surface having a plurality of predetermined surface indentations to enable the formation of a predetermined amount of controlled local turbulence adjacent the curvilinear interior surface to reduce friction and suppress noise the compressed air moves across the curvilinear interior surface, wherein the plenum member is formed as an irremovable part of the plenum chamber.

* * * * *